United States Patent
Al-Zahrani et al.

(10) Patent No.: US 7,256,319 B2
(45) Date of Patent: Aug. 14, 2007

(54) CATALYSTS FOR PRODUCTION OF OLEFINS BY OXIDATIVE DEHYDROGENATION, AND METHODS OF MAKING AND USING THE SAME

(75) Inventors: Saeed M. Al-Zahrani, Riyadh (SA); Ahmad E. Abasaeed, Riyadh (SA); Nimir O. Elbashir, Riyadh (SA); Mazhar A. Abdulwahed, Riyadh (SA)

(73) Assignee: Saudi Basic Industries Corporation, Riyadh (SA)

( * ) Notice: Subject to any disclaimer, the term of this patent is extended or adjusted under 35 U.S.C. 154(b) by 252 days.

(21) Appl. No.: 10/383,975

(22) Filed: Mar. 7, 2003

(65) Prior Publication Data

US 2003/0149323 A1  Aug. 7, 2003

Related U.S. Application Data

(63) Continuation of application No. 09/604,181, filed on Jun. 27, 2000, now abandoned.

(51) Int. Cl.
   *C07C 5/373* (2006.01)
   *C07C 5/333* (2006.01)

(52) U.S. Cl. .................................. 585/662; 585/658

(58) Field of Classification Search ............... 585/658, 585/662
   See application file for complete search history.

(56) References Cited

U.S. PATENT DOCUMENTS

| 3,933,933 A | 1/1976 | Bertus | 585/624 |
|---|---|---|---|
| 4,110,253 A | 8/1978 | Leach | 252/457 |
| 4,164,519 A | 8/1979 | Bertus | 585/622 |
| 4,474,897 A | 10/1984 | Hobbs | 502/242 |
| 5,162,597 A | 11/1992 | Wu | 585/646 |
| 5,468,710 A | 11/1995 | Regasco | 502/221 |
| 5,527,929 A | 6/1996 | Agaskar | 585/659 |
| 5,759,946 A | 6/1998 | Hoang | 502/303 |
| 5,852,219 A | 12/1998 | Sauer et al. | 568/71 |

FOREIGN PATENT DOCUMENTS

| EP | 0428413 | 5/1991 |
|---|---|---|
| EP | 0434546 | 6/1991 |
| EP | 0480594 | 4/1992 |
| EP | 0557790 | 9/1993 |
| EP | 0958860 A2 | 11/1999 |

OTHER PUBLICATIONS

European Search Report in EPO 01 112 978 dated Oct. 15, 2001.
ESP@CENET Database, Abstract of Japan Patent Publication No. 7010782, Jan. 13, 1995.

*Primary Examiner*—Thuan Dinh Dang
(74) *Attorney, Agent, or Firm*—William J. Spatz; Jim D. Wheelington

(57) ABSTRACT

The present invention provides a catalyst composition for the production of olefins by oxidative dehydrogenation of hydrocarbons, and of using such catalyst compositions. The catalysts of the present invention include compositions of the formula:

$$X_x Y_y W O_z$$

wherein X is at least one element selected from the group consisting of Li, Na, K, Rb, Cs, and Fr; Y is at least one element selected from the group consisting of B, Al, Ga, In, Ti, C, Si, Ge, Sn, and Pb; x is 0.5-2.5; y is 0.05-5; and z is the number of oxygen atoms required to satisfy the valancy of X, Y, and W in said composition. The methods and catalysts of the present invention are specifically useful for the combined production of propene and isobutene at relatively high conversion, selectivity, and productivity, and with minimal side products.

20 Claims, No Drawings

CATALYSTS FOR PRODUCTION OF OLEFINS BY OXIDATIVE DEHYDROGENATION, AND METHODS OF MAKING AND USING THE SAME

This application is a continuation of application 09/604,181, filed on Jun. 27, 2000, now abandoned.

BACKGROUND OF THE INVENTION

1. Field of the Invention

The present invention relates to new catalysts for the production of olefinic hydrocarbons by oxidative dehydrogenation and to methods of using the same. More particularly, this invention relates to tungsten-based catalysts for the oxidative dehydrogenation of hydrocarbons to yield olefins, and preferably, to the production of light olefins from light hydrocarbons.

2. Description of the Related Art

Several publications are referenced in this application. These references describe the state of the art to which this invention pertains, and are incorporated herein by reference.

Olefinic hydrocarbons, such as ethylene, propene, butene, and isobutene, are critical intermediates in the petrochemical industry. In order to satisfy market demand, substantial efforts have been invested in the production of such compounds by conventional catalytic dehydrogenation methods. For example, U.S. Pat. No. 5,468,710 to Resasco et al. describes the use of a composition containing sulfided nickel and non-acidic alumina as a catalyst for conventional dehydrogenation of organic compounds, such as isobutane, to yield the corresponding olefin.

However, conventional dehydrogenation has several disadvantages, including the need for high reaction temperatures (e.g., 550-650° C.), the deactivation of the catalyst by coke formation, and the consequent need for periodic catalyst regeneration at 20-30 minute intervals throughout the process. In addition, there are thermodynamic limitations on the activity of catalysts for conventional dehydrogenation. For example, such catalysts are only 85% selective at 45-50% isobutane conversion.

As a result of these substantial drawbacks, the petroleum industry has sought a solution to the demand for olefinic hydrocarbons in the use of oxidative dehydrogenation methods. Oxidative dehydrogenation is not subject to the problems associated with conventional dehydrogenation because of the presence of oxygen in the reaction mixture. However, to date, no commercial catalyst systems are available for oxidative dehydrogenation methods.

Various methods have been used to develop such a catalyst system. For example, U.S. Pat. Nos. 3,821,324; 3,933,933; and 4,164,519 describe oxidative dehydrogenation catalysts comprising titanium, at least one component selected from tungsten and molybdenum, and at least one additional component selected from phosphorus, bismuth, lead, antimony, and arsenic.

Japanese Patent Publication No. JP 07010782 describes the uses of an oxidative dehydrogenation catalyst to prepare isobutene and methacrolein. The catalyst contained molybdenum, iron, cobalt, cesium, silicon, bismuth, phosphorus, and nitrogen. A mixture of isobutane, oxygen, and nitrogen gas was passed through a reactor containing the mixed oxide catalyst at 440° C. to yield the corresponding olefins, isobutene, propene, and methacrolein, at a 3.8% conversion, with 13.9, 3.3, and 18.9% selectively, respectively. Similarly, Japanese Patent Publication No. JP 93150371 describes the use of alkali metal- and alkaline earth metal-containing catalysts for the preparation of isobutene and methacrolein from isobutane. The oxidative dehydrogenation catalysts and mixed oxide catalysts contained bismuth and molybdenum.

Japanese patent 3-218327 describes the oxidative dehydrogenation of propane or isobutane using a catalyst comprising either tin oxide and phosphorous oxide as the main components, or indium oxide and phosphorous oxide as the main components. However, the selectivity was only 32% at 1.4% conversion. Similarly, U.S. Pat. No. 5,759,946 describes a catalyst based on chromium oxide for oxidative dehydrogenation of hydrocarbons, and European Patent Publication No. EP 0557790 discloses the use of a catalyst containing phosphorous oxide for producing isobutene by oxidative dehydrogenation of isobutane. However, like the catalysts described above, these catalysts suffer from low selectivity and/or yield.

D. Stem and R. K. Grasselli (*J. Catal.*, Volume 167, pages 570-572 (1997)) disclose the use of several metal tungstate catalysts containing cobalt, nickel, iron, zinc, and cerium for the oxidative dehydrogenation of propane. A maximum yield of 9.1% was obtained using cobalt tungstate catalyst at a selectivity of 65.1% and at a reaction temperature of 560° C.

Sodium tungstate in combination with hydrogen peroxide was used as a catalyst for the epoxidation of unsaturated aldehydes and carboxylic acids (see EP 434546 and Ballisteri et al., *Stud. Org. Chem.*, Volume 33, pages 341-46 (1988)). This catalyst was also used for the epoxidation of a cyclohexene ring in various organic compounds (see also Japanese Patent Publication JP 62230778). However, to date, tungsten-based catalysts have not been used for olefin production by oxidative dehydrogenation of hydrocarbons at reasonably high selectivity.

In view of the foregoing, it is evident that the art has not succeeded in achieving high conversion at high selectivity, such that the yield of the desired olefin is maximized, as extraneous oxidative side reactions are minimized. None of the prior art references disclose or suggest tungsten-based catalysts which provide selective production of olefins from hydrocarbons by oxidative dehydrogenation. Accordingly, it would be desirable to produce a new catalyst for use in the selective production of olefins from hydrocarbons by oxidative dehydrogenation.

SUMMARY OF THE INVENTION

The present invention provides a new highly selective catalyst system for the production of olefins by oxidative dehydrogenation of hydrocarbons. The catalyst compositions of the present invention are particularly well suited for the catalytic preparation of light olefins from light hydrocarbons, e.g., the production of isobutene and propene from isobutane. Using the improved catalyst, isobutane is oxidatively dehydrogenated in the presence of molecular oxygen at relatively high levels of conversion, selectivity, and productivity, with minimal side products, at temperatures between 350° C. to 550° C. Further, the improved catalysts of the present invention can be used to produce isobutene and propene in combination at controllable ratios. Oxidative dehydrogenation using the improved catalysts can accommodate propane and isobutane as the feed stock, and product separation is less intensive because no partial oxidation product is formed. In addition, unreacted starting materials may be recycled after each separation step.

The catalyst compositions of the present invention include compositions of the formula:

$X_xY_yWO_z$ wherein:

X is at least one element selected from Li, Na, K, Rb, Cs, and Fr;

Y is at least one element selected from B, Al, Ga, In, Tl, Si, Ge, Sn, or Pb;

x is 0.5-2.5;

y is 0.05-5; and z is the number of oxygen atoms required to satisfy the valancy of X, Y and W in the formula. The catalysts are preferably produced using the methods disclosed herein.

DETAILED DESCRIPTION OF THE PREFERRED EMBODIMENTS

One aspect of the invention relates to a catalyst for the production of olefins from hydrocarbons via oxidative dehydrogenation. The catalyst composition comprises a composition of the formula:

$X_xY_yWO_z$ wherein:

X is one or more alkali metals (e.g., Li, Na, K, Rb, Cs, Fr);

Y is one or more elements selected from group IIIA (e.g., B, Al, Ga, In, Tl), and/or IVA (e.g., C, Si, Ge, Sn, Pb) of the periodic table;

x is 0.5 to 2.5;

y is 0.05 to 5; and z is the number of oxygen atoms needed to satisfy the valency requirements of the remaining elements in the compound.

The catalyst of the present invention is durable and recyclable and it can be used with or without a support or binder. Suitable supports for the catalyst include alumina, silica, titania, zirconia, zeolites, silicon carbide, molecular sieves and other microporous or nonporous materials, and mixtures thereof. The amount of support used can be adjusted based on the application requirements of the desired application.

Another aspect of the invention relates to methods of using the catalyst composition of the invention to produce olefins from hydrocarbons. In a preferred embodiment, the catalyst of the present invention may be used to produce light olefins, such as isobutene and propene at high selectivity, from light hydrocarbons, such as isobutane, in the presence of molecular oxygen at temperatures between 350° C. to 550° C.

Another preferred embodiment of the invention relates to an improved process for the combined catalytic preparation of isobutene and propene by the dehydrogenation of isobutane and propane in the presence of molecular oxygen at temperatures between 350° C. to 550° C., using the catalyst composition of the invention. In this regard, the method of the present invention facilitates product separation because no partial oxidation products are formed using the catalyst of the present invention. Additionally, the instant method allows unreacted starting materials to be recycled.

Preferably, the process achieves an isobutane conversion of at least 10% per cycle, more preferably at least 12%, even more preferably at least 15%, and most preferably at least 25%. In a further preferred embodiment, the selectivity in mol % for the production of olefins is greater than 80%, and more preferably greater than 90%. The yield of olefins in mol % per cycle is preferably greater than 10%, and more preferably greater than 20%. The total yield of olefins in mol % is preferably greater than 75%, more preferably greater than 80%, and most preferably greater than 85%.

The following examples are intended to be illustrative of this invention. They are, of course, not to be taken to in any way limit the scope of this invention. Numerous changes and modifications can be made with respect to the invention without departing from the spirit or scope of the present invention.

EXAMPLES

As used in the following examples, the terms below are defined as follows:

"W/F" is defined as the weight of the catalyst in grams divided by the flow rate of reactant stream in ml/sec measured at S.T.P.

"Isobutane ($I-C_4H_{10}$) conversion" is defined as:

[(Mols $I-C_4H_{10}$ in feed)−(Mols $I-C_4H_{10}$ in effluent)] ÷(Mols $I-C_4H_{10}$ in feed)]×100.

"Isobutene ($I-C_4H_8$) selectivity" is defined as:

[(Mols $I-C_4H_8$ in effluent)÷(Mols $I-C_4H_{10}$ converted)]×100.

"Isobutene ($I-C_4H_9$) yield" is defined as:

[(Mols $I-C_4H_8$ formed)÷(Mols $I-C_4H_{10}$ in feed)]×100.

Example 1

The catalyst used in this example had the empirical formula $Na_2Al_{3.8}WO_x$. It was prepared by dissolving the required amounts of sodium tungstate dihydrate (MERCK) in distilled water. Then alumina (γ-alumina, STREM CHEMICALS) was added slowly to the solution. This step led to a paste formation. The paste was then dried at 120° C., and calcined in air at 750° C.

Example 2

The catalyst used in this example had the empirical formula $Na_2Al_2WO_x$. The protocol used to make this catalyst was essentially the same as that described in Example 1 with the exception that the catalyst preparation contained a 1:1 molar ratio of sodium tungstate to alumina.

Example 3

The catalyst used in this example had the empirical formula $Na_2SiWO_x$. The protocol used to make this catalyst was the same as that described in Example 2, with the exception that fumed silica (having high surface area, 390 m²/gm, from SIGMA CHEMICAL CO.) was added instead of alumina to the tungstate solution.

Example 4

The catalyst formula and experimental procedure used to make the catalyst were essentially the same as that described in Example 3, with the exception that silicon dioxide (from SIGMA CHEMICAL CO.) was used instead of fumed silica.

Example 5

Calcined catalysts prepared in the Examples 1-4 were pressed into pellets and crushed to 20-40 mesh. The catalysts were tested in a fixed bed quartz reactor. In each test the catalyst was pretreated in a stream of oxygen and helium for one hour at 400° C. Then, the feed gas was passed through the reactor at the desired temperature.

The following conditions were employed:

| | |
|---|---|
| reaction temperature: | 500° C. |
| catalyst: | 1 gm |
| pressure: | atmospheric |
| W/F: | 0.8 sec. |
| Feed composition: | isobutane/oxygen/helium: 26.5/6.6/66.9 (mol %) |

After reaching a steady state, the reactor effluent was analyzed using a modern gas chromatograph (HP 6890), equipped with both FID (flame ionization detector) and TCD (thermal conductivity detector) detectors. Activity results were calculated according to the equations given above. Results are summarized below in Table 1.

TABLE 1

Activity results

| Example No. | X (%) | $(C_3H_6/$ $i\text{-}C_4H_8 + C_3H_6) \times 100$ | $i\text{-}C_4H_8$ Y | $i\text{-}C_4H_8$ S | $C_3H_6$ Y | $C_3H_6$ S | $i\text{-}C_4H_8 + C_3H_6$ Y | $i\text{-}C_4H_8 + C_3H_6$ S | $CH_4$ & $CO_x$ Y | $CH_4$ & $CO_x$ S |
|---|---|---|---|---|---|---|---|---|---|---|
| 1 | 18.0 | 25.3 | 12.6 | 69.8 | 4.2 | 23.6 | 16.8 | 93.4 | 1.2 | 6.6 |
| 2 | 25.8 | 34.3 | 16.0 | 62.1 | 8.3 | 32.4 | 24.4 | 94.5 | 1.4 | 5.5 |
| 3 | 12.1 | 28.6 | 8.2 | 70.0 | 3.4 | 28.0 | 11.9 | 98.0 | 0.2 | 2.0 |
| 4 | 14.8 | 31.7 | 11.2 | 66.9 | 4.5 | 31.0 | 14.5 | 97.9 | 0.3 | 2.1 |

X: $i\text{-}C_4H_{10}$-Conversion
Y: Yield in mol %
S: Selectivity in mol %
$CO_x$: Carbon dioxide and/or carbon monoxide From the results summarized above, it will be evident that each of the catalysts in Examples 1-4 exhibited high selectivity for isobutene. A considerable amount of propene was also formed in the reaction, which is desirable as well, due to the large demand for this intermediate. Total selectivity for isobutene and propene exceeds 93% at conversions higher than 12%. This finding is significant because the reaction was carried out at relatively high temperature and there was no ethylene or partial oxidation products formed. Propene formation is believed to occur by a consecutive disproportion reaction of isobutene, wherein 3 isobutene molecules give 4 propene molecules. This reaction was also demonstrated using isobutene as a feed stock. Propylene was found to be the exclusive useful product under the same conditions.

By decreasing the relative aluminum content from 3.8 to 2 in the catalyst (Examples 1 and 2), isobutane conversion increased from 18.0 to 25.8%, and isobutene yield increased consequently from 12.6 to 16.0%. Total olefin selectivity, towards isobutene and propene, and selectivity towards other products, i.e., CO, $CO_2$ and methane, remained nearly constant. In parallel, propene formation was enhanced. Based on these results, it can be concluded that by optimizing the aluminum content in the catalyst the reaction can be directed towards the desired propene to propene plus isobutene ratio.

When silica was used instead of alumina in the preparation of catalysts (Examples 3 and 4), total selectivity towards useful products, i.e. isobutene and propene, was enhanced to 98%. Thus, using different types of silica, i.e., different element sources or ingredients, as demonstrated in Examples 3 and 4, can desirably modify the catalyst behavior and the resultant propene to propene plus isobutene ratio. Preferably, the total selectivity for one or more olefins is increased to at least 95%.

The above description of the invention is intended to be illustrative and not limiting. Various changes or modifications in the embodiments described may occur to those skilled in the art. These can be made without departing from the spirit or scope of the invention.

The invention claimed is:

1. A method of producing olefin comprising contacting a hydrocarbon with a catalyst composition in the presence of molecular oxygen at 350° C. to 550° C., such that said hydrocarbon is oxidatively dehydrogenated to olefins, said catalyst composition comprising a supported or unsupported catalyst composition having the formula:

$$X_xY_yWO_z$$

wherein:
X is at least one element selected from the group consisting of Li, Na, K, Rb, Cs, and Fr;
Y is at least one element selected from the group consisting of Al and Si;
x is 0.5-2.5;
y is 0.05-5; and
z is the number of oxygen atoms required to satisfy the valancy of X, Y, and W in said catalyst composition.

2. The method of claim 1, wherein said hydrocarbon is selected from the group consisting of propane, n-butane, isobutane, and mixtures thereof, and said olefins are selected from the group consisting of propylene, n-butene, isobutene, and mixtures thereof.

3. The method of claim 2, wherein at least 10% of said hydrocarbons is converted to olefin per cycle.

4. The method of claim 2, wherein at least 15% of said hydrocarbons is converted to olefin per cycle.

5. The method of claim 2, wherein at least 25% of said hydrocarbons is converted to olefin per cycle.

6. The method of claim 2, wherein said method achieves at least 80 mol % selectivity for the production of olefins.

7. The method of claim 2, wherein said method achieves at least 90 mol % selectivity for the production of olefins.

8. The method of claim 2, wherein said method achieves at least 10 mol % yield of olefin per cycle.

9. The method of claim 2, wherein said method achieves at least 20 mol % yield of olefin per cycle.

10. The method of claim 2, wherein said method achieves a total yield of olefins of at least 75 mol %.

11. The method of claim 2, wherein said method achieves a total yield of olefins of at least 85 mol %.

12. The method of claim 2, wherein said hydrocarbon is isobutane and said olefins are a mixture of propene and isobutene.

13. The method of claim 1, wherein Y is Al.

14. The method of claim 13, wherein said olefins are propene and isobutene.

15. The method of claim 1, wherein the catalyst composition comprises a support.

16. The method of claim 15, wherein the support comprises a silica support and the method achieves at least 95 mol % selectivity for the production of olefins.

17. A method of producing olefin from a hydrocarbon comprising contacting the hydrocarbon with a catalyst composition in the presence of molecular oxygen at 350° C. to 550° C., such that said hydrocarbon is oxidatively dehydrogenated to olefins with a selectivity toward olefins which exceeds 97% on a molar basis, said catalyst composition having the formula:

$$X_xSi_yWO_z$$

wherein:
X is at least one element selected from the group consisting of Li, Na, K, Rb. Cs, and Fr;
x is 0.5-2.5;
y is 0.05-5; and
z is the number of oxygen atoms required to satisfy the valancy of X, Si and W in said catalyst composition.

18. The method of claim 17, wherein said olefins are propene and isobutene.

19. A method of producing olefin from a hydrocarbon comprising contacting the hydrocarbon with a catalyst composition in the presence of molecular oxygen at 350° C. to 550° C., such that said hydrocarbon is oxidatively dehydrogenated with a selectivity toward olefins which exceeds 95% on a molar basis, said catalyst composition having the formula:

$$X_xSi_yWO_z$$

wherein:
X is at least one element selected from the group consisting of Li, Na, K, Rb, Cs, and Fr;
x is 0.5-2.5;
y is 0.05-5; and
z is the number of oxygen atoms required to satisfy the valancy of X, Si and W in said catalyst composition.

20. The method of claim 19, wherein said catalyst composition further comprises a silica support and said olefins comprise propene and/or isobutene.

* * * * *